US011964259B2

(12) United States Patent
Chen et al.

(10) Patent No.: US 11,964,259 B2
(45) Date of Patent: Apr. 23, 2024

(54) CATALYST COMPOSITION FOR HYDROGENATING 4,4'-METHYLENEDIANILINE DERIVATIVES AND METHOD FOR PREPARING 4,4'-METHYLENE BIS(CYCLOHEXYLAMINE) DERIVATIVES USING THE SAME

(71) Applicant: INDUSTRIAL TECHNOLOGY RESEARCH INSTITUTE, Hsinchu (TW)

(72) Inventors: Chao-Huang Chen, Hsinchu (TW); Jyun-Da Wu, Xinfeng Township (TW); Tzong-Shyan Lu, Houlong Township (TW); Ying-Chieh Lee, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 751 days.

(21) Appl. No.: 17/135,515

(22) Filed: Dec. 28, 2020

(65) Prior Publication Data

US 2021/0197177 A1   Jul. 1, 2021

Related U.S. Application Data

(63) Continuation-in-part of application No. 16/731,783, filed on Dec. 31, 2019, now abandoned.

(51) Int. Cl.
| | |
|---|---|
| *C07C 209/72* | (2006.01) |
| *B01J 8/02* | (2006.01) |
| *B01J 21/10* | (2006.01) |
| *B01J 23/46* | (2006.01) |
| *B01J 35/61* | (2024.01) |
| *B01J 37/02* | (2006.01) |

(52) U.S. Cl.
CPC ........... *B01J 23/464* (2013.01); *B01J 8/0242* (2013.01); *B01J 21/10* (2013.01); *B01J 35/615* (2024.01); *B01J 37/0234* (2013.01); *C07C 209/72* (2013.01); *B01J 2523/821* (2013.01); *B01J 2523/822* (2013.01)

(58) Field of Classification Search
None
See application file for complete search history.

(56) References Cited

U.S. PATENT DOCUMENTS

| 1,827,129 | A | 9/1933 | Lommel et al. |
|---|---|---|---|
| 2,092,525 | A | 9/1937 | Adkins et al. |
| 2,129,831 | A | 9/1938 | Winans et al. |
| 2,132,389 | A | 10/1938 | Bertsch et al. |
| 2,511,028 | A | 6/1950 | Whitman et al. |
| 2,606,927 | A | 8/1952 | Barkdoll et al. |
| 3,347,917 | A | 10/1967 | Arthur et al. |
| 3,591,635 | A | 7/1971 | Farrissey et al. |
| 3,644,522 | A | 2/1972 | Brake et al. |
| 3,914,307 | A | 10/1975 | Massie et al. |
| 4,448,995 | A | 5/1984 | Allen |
| 4,754,070 | A | 6/1988 | Casey et al. |
| 5,026,914 | A | 6/1991 | Jenkins et al. |
| 5,545,756 | A | 8/1996 | Vedage et al. |
| 6,504,060 | B1 | 1/2003 | Bunnenberg et al. |
| 6,998,507 | B1 | 2/2006 | Ding et al. |
| 7,091,384 | B2 | 8/2006 | Jaeger et al. |
| 8,722,922 | B2 | 5/2014 | Chang et al. |
| 9,399,615 | B2 | 7/2016 | Chen et al. |
| 9,580,380 | B2 | 2/2017 | Li et al. |
| 2004/0034252 | A1* | 2/2004 | Stochniol ............... B01J 23/462 564/450 |

FOREIGN PATENT DOCUMENTS

| CN | 1461746 A | 12/2003 |
|---|---|---|
| CN | 102030657 A | 4/2011 |
| CN | 106029638 A | 10/2016 |
| EP | 0 324 190 A2 | 7/1989 |
| TW | 201619099 A | 6/2016 |

OTHER PUBLICATIONS

Taiwanese Office Action and Search Report for Taiwanese Application No. 109146453, dated Jun. 23, 2021.

* cited by examiner

*Primary Examiner* — Sudhakar Katakam
*Assistant Examiner* — Jennifer C Sawyer
(74) *Attorney, Agent, or Firm* — Birch, Stewart, Kolasch & Birch, LLP

(57) ABSTRACT

A catalyst composition for hydrogenating 4,4'-methylenedianiline derivatives is provided. The catalyst composition includes a carrier including aluminum oxide and magnesium oxide, a rhodium-ruthenium active layer loaded on the surface of the carrier, and a solvent including an organic amine. The weight percentage of magnesium oxide in the carrier is between 12% and 30%. A method for preparing 4,4'-methylene bis(cyclohexylamine) derivatives using the catalyst composition is also provided.

20 Claims, No Drawings

CATALYST COMPOSITION FOR HYDROGENATING 4,4'-METHYLENEDIANILINE DERIVATIVES AND METHOD FOR PREPARING 4,4'-METHYLENE BIS(CYCLOHEXYLAMINE) DERIVATIVES USING THE SAME

TECHNICAL FIELD

The present disclosure relates to a catalyst composition, and more particularly to a catalyst composition for hydrogenating 4,4'-methylenedianiline (MDA) derivatives and a method for preparing 4,4'-methylene bis(cyclohexylamine) (PACM) derivatives using the same.

BACKGROUND 4,4'-methylenedianiline (abbreviated as MDA) is an important aromatic diamine compound, which is formed by the polymerization of aniline and formaldehyde and can be used to prepare methylene diphenyl diisocyanate (abbreviated as MDI) (a monomer to prepare polyurethane (PU)) or be reacted with maleic anhydride to prepare N,N'-(4,4'-diphenylmethane) bismaleimide. It can also be used as an epoxy resin hardener for composite materials.

After MDA is hydrogenated (that is, the benzene rings in the molecule are completely hydrogenated), 4,4'-methylene bis(cyclohexylamine) also called bis(para-amino cyclohexyl)methane (referred to as PACM or H12MDA) is obtained. The isocyanate (H12MDI) prepared from PACM as a raw material has good optical stability (anti-yellowing), weather resistance and mechanical properties. It can be used in the preparation of weather-resistant coatings, water-based PU fabrics, and thermoplastic polyurethanes (TPU). It can also be used as an epoxy resin hardener for high-strength and high-temperature-resistant composite materials, as well as for low-dielectric-constant electronic packaging materials.

SUMMARY

In accordance with one embodiment of the present disclosure, a catalyst composition for hydrogenating 4,4'-methylenedianiline derivatives is provided, including a carrier including aluminum oxide and magnesium oxide, wherein the weight percentage of the magnesium oxide in the carrier is in a range from 12% to 30%; a rhodium-ruthenium active layer loaded on the surface of the carrier; and a solvent including an organic amine.

In accordance with one embodiment of the present disclosure, a method for preparing 4,4'-methylene bis(cyclohexylamine) derivatives is provided, including placing the disclosed catalyst composition for hydrogenating 4,4'-methylenedianiline derivatives in a reactor; and introducing 4,4'-methylenedianiline (MDA) derivatives and hydrogen into the reactor to proceed a hydrogenation reaction to prepare 4,4'-methylene bis(cyclohexylamine) (PACM) derivatives.

A detailed description is given in the following embodiments.

DETAILED DESCRIPTION

In order to improve the selectivity of synthesis of bis (para-amino cyclohexyl)methane (PACM) derivatives, the present disclosure provides a novel catalyst composition and a method for preparing 4,4'-methylene bis(cyclohexylamine) (PACM) derivatives using the same. By increasing the content of magnesium oxide in the catalyst system and using an organic amine solvent for the hydrogenation reaction, on the one hand, the by-products generated by the product self-coupling reaction are avoided, and on the other hand, the selectivity of synthetic of 4,4'-methylene bis(cyclohexylamine) (PACM) derivatives is also greatly improved, and the contents of carbon monoxide (CO) and methane ($CH_4$) in the tail gas can be effectively reduced. In accordance with one embodiment of the present disclosure, a catalyst composition for hydrogenating 4,4'-methylenedianiline derivatives is provided, including a carrier including aluminum oxide and magnesium oxide, wherein the weight percentage of the magnesium oxide in the carrier is in a range from 12% to 30%; a rhodium-ruthenium active layer loaded on the surface of the carrier; and a solvent including an organic amine. The content of the magnesium oxide has a certain relationship with the characteristics (acidity/alkalinity degree) of the carrier. Generally speaking, the alkalinity of the carrier increases as the content of the magnesium oxide increases. With a proper proportion of the content of the magnesium oxide, a better reactivity, product selectivity and catalyst mechanical strength will be obtained. In the present disclosure, the 4,4'-methylenedianiline derivatives mean substituted or unsubstituted 4,4'-methylenedianiline.

In one embodiment, the specific surface area of the carrier is in a range from about 150 $m^2/g$ to about 250 $m^2/g$. In one embodiment, the weight percentage of the magnesium oxide in the carrier is in a range from about 14% to about 25%. In one embodiment, the concentration of the magnesium oxide exhibits a decreasing gradient distribution from the surface to the interior of the carrier. In one embodiment, the interior of the carrier mainly consists of the aluminum oxide ($Al_2O_3$), and the surface of the carrier mainly consists of magnesium aluminum oxide (Mg(Al)O), wherein the concentration of the magnesium oxide exhibits a decreasing gradient distribution from the surface to the interior of the carrier. The "magnesium aluminum oxide" mentioned in the present disclosure refers to a composite oxide of the aluminum oxide and the magnesium oxide. In one embodiment, the weight ratio between the magnesium oxide and the aluminum oxide in the magnesium aluminum oxide (Mg(Al)O) is in a range from about 2:1 to about 1:2. In one embodiment, the weight percentage of the magnesium aluminum oxide in the carrier is in a range from about 20% to about 50%.

In one embodiment, the weight ratio between the rhodium and the ruthenium in the rhodium-ruthenium active layer is in a range from about 40:60 to about 10:90. In one embodiment, the weight ratio between the rhodium-ruthenium active layer and the carrier is in a range from about 1:24 to about 1:16. In one embodiment, the organic amine may include aniline, cyclohexylamine, dicyclohexylamine, o-toluidine, 2-methylaniline, 2-methylcyclohexylamine, 2,6-dimethylaniline, 2,6-dimethylcyclohexylamine, 2-ethyl-6-methylaniline, 2-ethyl-6-methyl cyclohexylamine, 4,4'-methylene bis(cyclohexylamine) derivatives, or a combination thereof. In one embodiment, the 4,4'-methylene bis (cyclohexylamine) derivatives are represented by formula (I):

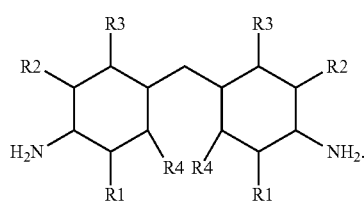

In formula (I), R1, R2, R3 and R4, independently, include H, CH$_3$, C$_2$H$_5$ or C$_3$H$_7$. In one embodiment, the solvent of the disclosed catalyst composition further includes tetrahydrofuran (THF). In one embodiment, the weight ratio of the organic amine in the solvent is about 2.5 wt % to 100 wt %. In one embodiment, the solvent of the disclosed catalyst composition does not contain tetrahydrofuran (THF), alcohols, ethers, or other organic solvents, which can effectively reduce the content of gas by-products such as carbon monoxide (CO) or methane (CH$_4$) in tail gas.

In accordance with one embodiment of the present disclosure, a method for preparing 4,4'-methylene bis(cyclohexylamine) derivatives is provided, including placing a catalyst composition for hydrogenating 4,4'-methylenedianiline derivatives in a reactor; and introducing 4,4'-methylenedianiline (MDA) derivatives and hydrogen into the reactor to proceed to a hydrogenation reaction to prepare 4,4'-methylene bis(cyclohexylamine) (PACM) derivatives.

In one embodiment, the catalyst composition for hydrogenating 4,4'-methylenedianiline derivatives may include a carrier, a rhodium-ruthenium active layer and a solvent including an organic amine. The carrier may include aluminum oxide and magnesium oxide, and the weight percentage of the magnesium oxide in the carrier is in a range from about 12% to about 30%. The rhodium-ruthenium active layer is loaded on the surface of the carrier.

In one embodiment, the specific surface area of the carrier is in a range from about 150 m$^2$/g to about 250 m$^2$/g. In one embodiment, the weight percentage of the magnesium oxide in the carrier is in a range from about 14% to about 25%. In one embodiment, the concentration of the magnesium oxide exhibits a decreasing gradient distribution from the surface to the interior of the carrier. In one embodiment, the interior of the carrier mainly consists of the aluminum oxide (Al$_2$O$_3$), and the surface of the carrier mainly consists of magnesium aluminum oxide (Mg(Al)O), wherein the concentration of the magnesium oxide exhibits a decreasing gradient distribution from the surface to the interior of the carrier. In one embodiment, the weight ratio between the magnesium oxide and the aluminum oxide in the magnesium aluminum oxide (Mg(Al)O) is in a range from about 2:1 to about 1:2. In one embodiment, the weight percentage of the magnesium aluminum oxide in the carrier is in a range from about 20% to about 50%.

In one embodiment, the weight ratio between the rhodium and the ruthenium in the rhodium-ruthenium active layer is in a range from about 40:60 to about 10:90. In one embodiment, the weight ratio between the rhodium-ruthenium active layer and the carrier is in a range from about 1:24 to about 1:16. In one embodiment, the organic amine may include aniline, cyclohexylamine, dicyclohexylamine, o-toluidine, 2-methylaniline, 2-methylcyclohexylamine, 2,6-dimethylaniline, 2,6-dimethylcyclohexylamine, 2-ethyl-6-methylaniline, 2-ethyl-6-methyl cyclohexylamine, 4,4'-methylene bis(cyclohexylamine) derivatives, or a combination thereof. In one embodiment, the 4,4'-methylene bis(cyclohexylamine) derivatives are represented by formula (I):

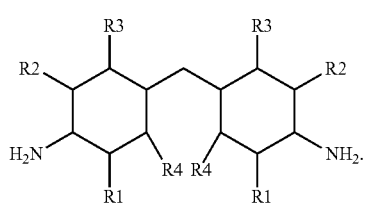

In formula (I), R1, R2, R3 and R4, independently, include H, CH$_3$, C$_2$H$_5$ or C$_3$H$_7$. In one embodiment, the solvent of the disclosed catalyst composition further includes tetrahydrofuran (THF). In one embodiment, the weight ratio of the organic amine in the solvent is about 2.5 wt % to 100 wt %. In one embodiment, the solvent of the disclosed catalyst composition does not contain tetrahydrofuran (THF), alcohols, ethers, or other organic solvents.

In one embodiment, the reactor may include a continuous reactor. In one embodiment, the reactor may include a trickle-bed reactor, a bubble-cap column reactor, or a loop reactor. In one embodiment, the hydrogen pressure of the hydrogenation reaction is in a range from about 60 bar to about 80 bar. In one embodiment, the temperature of the hydrogenation reaction is in a range from about 100° C. to about 160° C. If the reaction temperature is too high, the ratio of trans-trans isomers of the products may thus be too high.

In one embodiment, the 4,4'-methylenedianiline derivatives (the reactants of the hydrogenation reaction) are represented by formula (II):

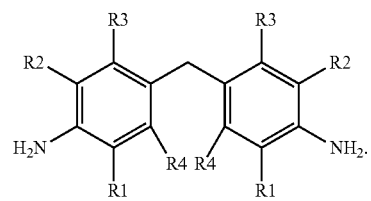

In formula (II), R1, R2, R3 and R4, independently, include H, CH$_3$, C$_2$H$_5$ or C$_3$H$_7$. In one embodiment, the 4,4'-methylenedianiline derivatives include 4,4'-methylenedianiline (MDA), 3,3'-dimethyl-4,4'-diaminodiphenylmethane (MDT) or 4,4'-methylene-bis(2-methyl-6-ethylaniline) (MED). In one embodiment, the 4,4'-methylene bis(cyclohexylamine) derivatives (the products of the hydrogenation reaction) are represented by formula (I):

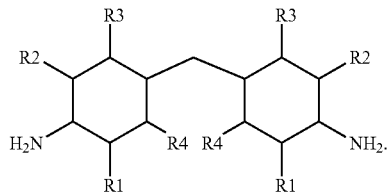

In formula (I), R1, R2, R3 and R4, independently, include H, CH$_3$, C$_2$H$_5$ or C$_3$H$_7$. In one embodiment, the 4,4'-methylene bis(cyclohexylamine) derivatives include 4,4'-methylene bis(cyclohexylamine) (PACM), 3,3'-dimethyl-4,4'-methylene bis(cyclohexylamine) (DMDC) or hydrogenated 4,4'-methylene-bis(2-methyl-6-ethyl aniline) (H-MED)

The present disclosure adopts a novel catalyst hydrogenation process. By increasing the content of magnesium oxide in the catalyst system and using organic amine solvents, and in a continuous reactor, under a relatively low pressure condition (within 80 bar), a continuous hydrogenation reaction of 4,4'-methylenedianiline (MDA) derivatives is carried out to produce liquid 4,4'-methylene bis(cyclohexylamine) (PACM) derivatives. The yield can reach more than 90%, and the ratio of trans-trans isomers of 4,4'-methylene bis(cyclohexylamine) (PACM) derivatives is less than 30%. At the same time, the tail gas contains only a small amount of catalyst-poison gases such as carbon monoxide (CO). The present disclosure uses a dual metal catalyst of ruthenium (Ru) and rhodium (Rh) loaded on the carrier containing magnesium oxide and aluminum oxide, and utilizes liquid organic amines, such as cyclohexylamine, aniline or self-product of 4,4'-methylene bis(cyclohexylamine) (PACM) derivatives, as a base source in the system and as a solvent. In the disclosed hydrogenation process, it is not easy to generate self-coupling by-products and gas by-products such as carbon monoxide (CO) or methane ($CH_4$), greatly reducing the consumption of raw materials and eliminating (gas/liquid) purification processes, and improving economy. Also, the hydrogen introduced in the process can be directly recovered and recycled, reducing investment costs and increasing competitiveness.

Preparation Example 1

Preparation of Catalyst A

First, 2.6 L of deionized aqueous solution containing 258 g of magnesium nitrate and 377 g of aluminum nitrate was added to 2 L deionized aqueous solution containing 118 g of sodium hydroxide and 256 g of sodium carbonate with stirring at room temperature and aged for 18 hours to form magnesium-aluminum sol-gel (Mg—Al sol-gel). Next, 255 g of aluminum oxide (purchased from UOP, with a specific surface area of 188 $m^2/g$ and a pore volume of 0.87 ml/g) was added to the sol-gel with continuously stirring for 1 hour and filtered. The obtained filter cake was washed three times with water and then dried at 110° C. The dried filter cake was pulverized to less than 100 mesh to obtain modified aluminum oxide powder. Next, the modified aluminum oxide powder, an adhesive and water were mixed uniformly, extruded into strips, dried at 110° C., and calcined at 450° C. After pelletizing, the carrier was obtained. The content of the magnesium oxide in the carrier was approximately 9.6%.

15-20 g of the carrier was impregnated in a 4-fold amount of an impregnation solution (that is, 60-80 g) for 40 minutes. The impregnation solution was prepared with ruthenium nitrate ($Ru(NO_3)_3$) and rhodium nitrate ($Rh(NO_3)_3$) as precursors. After an appropriate amount of deionized water was added, the impregnation solution having a specific metal concentration (4% Ru, 1% Rh) was prepared. The impregnated catalyst was filtered, dried and calcined at 450° C. for 4 hours to obtain catalyst A prepared in this preparation example.

Preparation Example 2

Preparation of Catalyst B

First, 2.6 L of deionized aqueous solution containing 310 g of magnesium nitrate and 301 g of aluminum nitrate was added to 2 L deionized aqueous solution containing 118 g of sodium hydroxide and 256 g of sodium carbonate with stirring at room temperature and aged for 18 hours to form magnesium-aluminum sol-gel (Mg—Al sol-gel). Next, 205 g of aluminum oxide (purchased from UOP, with a specific surface area of 188 $m^2/g$ and a pore volume of 0.87 ml/g) was added to the sol-gel with continuously stirring for 1 hour and filtered. The obtained filter cake was washed three times with water and then dried at 110° C. The dried filter cake was pulverized to less than 100 mesh to obtain modified aluminum oxide powder. Next, the modified aluminum oxide powder, an adhesive and water were mixed uniformly, extruded into strips, dried at 110° C., and calcined at 450° C. After pelletizing, the carrier was obtained. The content of the magnesium oxide in the carrier was approximately 14.2%.

15-20 g of the carrier was impregnated in a 4-fold amount of an impregnation solution (that is, 60-80 g) for 40 minutes. The impregnation solution was prepared with ruthenium nitrate ($Ru(NO_3)_3$) and rhodium nitrate ($Rh(NO_3)_3$) as precursors. After an appropriate amount of deionized water was added, the impregnation solution having a specific metal concentration (4% Ru, 1% Rh) was prepared. The impregnated catalyst was filtered, dried and calcined at 450° C. for 4 hours to obtain catalyst B prepared in this preparation example.

Preparation Example 3

Preparation of Catalyst C

First, 2.6 L of deionized aqueous solution containing 258 g of magnesium nitrate and 377 g of aluminum nitrate was added to 2 L deionized aqueous solution containing 118 g of sodium hydroxide and 256 g of sodium carbonate with stirring at room temperature and aged for 18 hours to form magnesium-aluminum sol-gel (Mg—Al sol-gel). Next, 102 g of aluminum oxide (purchased from UOP, with a specific surface area of 188 $m^2/g$ and a pore volume of 0.87 ml/g) was added to the sol-gel with continuously stirring for 1 hour and filtered. The obtained filter cake was washed three times with water and then dried at 110° C. The dried filter cake was pulverized to less than 100 mesh to obtain modified aluminum oxide powder. Next, the modified aluminum oxide powder, an adhesive and water were mixed uniformly, extruded into strips, dried at 110° C., and calcined at 450° C. After pelletizing, the carrier was obtained. The content of the magnesium oxide in the carrier was approximately 18.9%.

15-20 g of the carrier was impregnated in a 4-fold amount of an impregnation solution (that is, 60-80 g) for 40 minutes. The impregnation solution was prepared with ruthenium nitrate ($Ru(NO_3)_3$) and rhodium nitrate ($Rh(NO_3)_3$) as precursors. After an appropriate amount of deionized water was added, the impregnation solution having a specific metal concentration (4% Ru, 1% Rh) was prepared. The impregnated catalyst was filtered, dried and calcined at 450° C. for 4 hours to obtain catalyst C prepared in this preparation example.

Preparation Example 4

Preparation of Catalyst D

First, 2.6 L of deionized aqueous solution containing 281 g of magnesium nitrate and 206 g of aluminum nitrate was added to 2 L deionized aqueous solution containing 118 g of sodium hydroxide and 256 g of sodium carbonate with stirring at room temperature and aged for 18 hours to form magnesium-aluminum sol-gel (Mg—Al sol-gel). Next, 100 g of aluminum oxide (purchased from UOP, with a specific surface area of 218 $m^2/g$ and a pore volume of 0.51 ml/g) was added to the sol-gel with continuously stirring for 1 hour and filtered. The obtained filter cake was washed three times with water and then dried at 110° C. The dried filter cake was pulverized to less than 100 mesh to obtain modified aluminum oxide powder. Next, the modified aluminum oxide powder, an adhesive and water were mixed uniformly, extruded into strips, dried at 110° C., and calcined at 450° C. After pelletizing, the carrier was obtained. The content of the magnesium oxide in the carrier was approximately 23.8%.

15-20 g of the carrier was impregnated in a 4-fold amount of an impregnation solution (that is, 60-80 g) for 40 minutes. The impregnation solution was prepared with ruthenium nitrate (Ru(NO$_3$)$_3$) and rhodium nitrate (Rh(NO$_3$)$_3$) as precursors. After an appropriate amount of deionized water was added, the impregnation solution having a specific metal concentration (4% Ru, 1% Rh) was prepared. The impregnated catalyst was filtered, dried and calcined at 450° C. for 4 hours to obtain catalyst D prepared in this preparation example.

Example 1

Preparation and Product Analysis of 4,4'-Methylene Bis(Cyclohexylamine)

First, 7 mL of catalyst B (20-30 mesh) prepared in Preparation Example 2 was weighed, which contained 4.0% Ru and 1.0% Rh. Next, the catalyst was placed in a fixed-bed reactor, and 4,4'-methylenedianiline (MDA) was hydrogenated in a continuous trickle-bed mode to prepare 4,4'-methylene bis(cyclohexylamine) (PACM).

The conditions of the hydrogenation reaction were as follows: Cyclohexylamine (CHA) was used as a solvent. The concentration of 4,4'-methylenedianiline (MDA) (MDA$_{100}$;

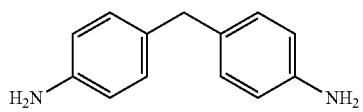 [SMILES: Nc1ccc(Cc2ccc(N)cc2)cc1]

) (purchased from Shuang Bang Industrial Corp.) was 25.0 wt %. The liquid flow rate was 4.5 mL/h. The reaction temperature was 130° C. The reaction pressure was 70-75 bar. The hydrogen flow rate was 80-100 mL/m.

The analysis results of the gas chromatography analyzer were as follows: The conversion rate of 4,4'-methylenedianiline (MDA) was 100% (no monocyclic hydrogenated intermediate (H6MDA)). The yield of 4,4'-methylene bis(cyclohexylamine) (PACM) was 92-94%, wherein the ratio of (trans, trans)-PACM was approximately 25%. The ratio of the self-coupling by-products was 0% (GC retention time at 40 minutes). The ratio of the coupling by-products of the products and cyclohexylamine was 3-5% (GC retention time at 25 minutes). The selectivity of 4,4'-methylene bis(cyclohexylamine) (PACM) prepared in this example was 86-90%.

The analysis of the tail gas was as follows: Carbon monoxide (CO) was about 2 ppm, and methane gas (CH$_4$) was about 0.03%. The above hydrogenation reaction conditions, gas chromatography analysis results and tail gas analysis results are shown in Table 1.

Example 2

Preparation and Product Analysis of 4,4'-Methylene Bis(Cyclohexylamine)

First, 7 mL of catalyst C (20-30 mesh) prepared in Preparation Example 3 was weighed, which contained 4.0% Ru and 1.0% Rh. Next, the catalyst was placed in a fixed-bed reactor, and 4,4'-methylenedianiline (MDA) was hydrogenated in a continuous trickle-bed mode to prepare 4,4'-methylene bis(cyclohexylamine) (PACM).

The conditions of the hydrogenation reaction were as follows: Cyclohexylamine (CHA) was used as a solvent. The concentration of 4,4'-methylenedianiline (MDA) (MDA$_{100}$;

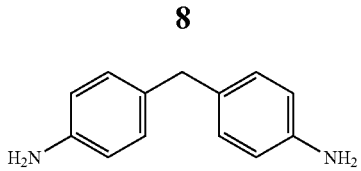

) (purchased from Shuang Bang Industrial Corp.) was 25.0 wt %. The liquid flow rate was 4.5 mL/h. The reaction temperature was 130° C. The reaction pressure was 70-75 bar. The hydrogen flow rate was 80-100 mL/m.

The analysis results of the gas chromatography analyzer were as follows: The conversion rate of 4,4'-methylenedianiline (MDA) was 100% (no monocyclic hydrogenated intermediate (H6MDA)). The yield of 4,4'-methylene bis(cyclohexylamine) (PACM) was about 94%, wherein the ratio of (trans, trans)-PACM was approximately 25%. The ratio of the self-coupling by-products was 0% (GC retention time at 40 minutes). The ratio of the coupling by-products of the products and cyclohexylamine was 2-3% (GC retention time at 25 minutes). The selectivity of 4,4'-methylene bis(cyclohexylamine) (PACM) prepared in this example was greater than 90%.

The analysis of the tail gas was as follows: Carbon monoxide (CO) was about 2 ppm, and methane gas (CH$_4$) was about 0.03%. The above hydrogenation reaction conditions, gas chromatography analysis results and tail gas analysis results are shown in Table 1.

Example 3

Preparation and Product Analysis of 4,4'-Methylene Bis(Cyclohexylamine)

First, 7 mL of catalyst D (20-30 mesh) prepared in Preparation Example 4 was weighed, which contained 4.0% Ru and 1.0% Rh. Next, the catalyst was placed in a fixed-bed reactor, and 4,4'-methylenedianiline (MDA) was hydrogenated in a continuous trickle-bed mode to prepare 4,4'-methylene bis(cyclohexylamine) (PACM).

The conditions of the hydrogenation reaction were as follows: Cyclohexylamine (CHA) was used as a solvent. The concentration of 4,4'-methylenedianiline (MDA) (MDA$_{100}$;

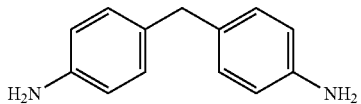

) (purchased from Shuang Bang Industrial Corp.) was 25.0 wt %. The liquid flow rate was 4.5 mL/h. The reaction temperature was 130° C. The reaction pressure was 70-75 bar. The hydrogen flow rate was 80-100 mL/m.

The analysis results of the gas chromatography analyzer were as follows: The conversion rate of 4,4'-methylenedianiline (MDA) was 100% (no monocyclic hydrogenated intermediate (H6MDA)). The yield of 4,4'-methylene bis(cyclohexylamine) (PACM) was about 95%, wherein the ratio of (trans, trans)-PACM was approximately 25%. The ratio of the self-coupling by-products was 0% (GC retention time at 40 minutes). The ratio of the coupling by-products of the products and cyclohexylamine was about 2% (GC retention time at 25 minutes). The selectivity of 4,4'-methylene bis(cyclohexylamine) (PACM) prepared in this example was greater than 90%.

The analysis of the tail gas was as follows: Carbon monoxide (CO) was about 2 ppm, and methane gas (CH$_4$) was about 0.03%. The above hydrogenation reaction conditions, gas chromatography analysis results and tail gas analysis results are shown in Table 1.

Example 4

Preparation and Product Analysis of 4,4'-Methylene Bis(Cyclohexylamine)

First, 7 mL of catalyst C (20-30 mesh) prepared in Preparation Example 3 was weighed, which contained 4.0% Ru and 1.0% Rh. Next, the catalyst was placed in a fixed-bed reactor, and 4,4'-methylenedianiline (MDA) was hydrogenated in a continuous trickle-bed mode to prepare 4,4'-methylene bis(cyclohexylamine) (PACM).

The conditions of the hydrogenation reaction were as follows: 4,4'-methylene bis(cyclohexylamine) (PACM) was used as a solvent. The concentration of 4,4'-methylenedianiline (MDA) (MDA$_{100}$;

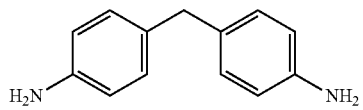 [SMILES: Nc1ccc(Cc2ccc(N)cc2)cc1]

) (purchased from Shuang Bang Industrial Corp.) was 25.0 wt %. The liquid flow rate was 4.5 mL/h. The reaction temperature was 130° C. The reaction pressure was 70-75 bar. The hydrogen flow rate was 80-100 mL/m.

The analysis results of the gas chromatography analyzer were as follows: The conversion rate of 4,4'-methylenedianiline (MDA) was 100% (no monocyclic hydrogenated intermediate (H6MDA)). The yield of 4,4'-methylene bis(cyclohexylamine) (PACM) was about 96-98%, wherein the ratio of (trans, trans)-PACM was approximately 27%. The ratio of the self-coupling by-products was 0% (GC retention time at 40 minutes). The ratio of the coupling by-products of the products and cyclohexylamine was 0% (GC retention time at 25 minutes). The selectivity of 4,4'-methylene bis(cyclohexylamine) (PACM) prepared in this example was greater than 95%.

The analysis of the tail gas was as follows: Carbon monoxide (CO) was about 2 ppm, and methane gas (CH$_4$) was about 0.03%. The above hydrogenation reaction conditions, gas chromatography analysis results and tail gas analysis results are shown in Table 1.

Comparative Example 1

Preparation and Product Analysis of 4,4'-Methylene Bis(Cyclohexylamine)

First, 7 mL of catalyst A (20-30 mesh) prepared in Preparation Example 1 was weighed, which contained 4.0% Ru and 1.0% Rh (the weight ratio relative to the carrier). Next, the catalyst was placed in a fixed-bed reactor, and 4,4'-methylenedianiline (MDA) was hydrogenated in a continuous trickle-bed mode to prepare 4,4'-methylene bis(cyclohexylamine) (PACM).

The conditions of the hydrogenation reaction were as follows: Cyclohexylamine (CHA) was used as a solvent. The concentration of 4,4'-methylenedianiline (MDA) (MDA$_{100}$;

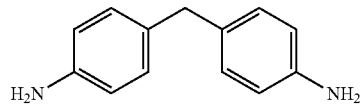

) (purchased from Shuang Bang Industrial Corp.) was 25.0 wt %. The liquid flow rate was 4.5 mL/h. The reaction temperature was 130° C. The reaction pressure was 70-75 bar. The hydrogen flow rate was 80-100 mL/m.

The analysis results of the gas chromatography analyzer were as follows: The conversion rate of 4,4'-methylenedianiline (MDA) was 100% (no monocyclic hydrogenated intermediate (H6MDA)). The yield of 4,4'-methylene bis(cyclohexylamine) (PACM) was 75-80%, wherein the ratio of (trans, trans)-PACM was approximately 25%. The ratio of the self-coupling by-products was 0% (GC retention time at 40 minutes). The ratio of the coupling by-products of the products and cyclohexylamine was 10-16% (GC retention time at 25 minutes). The selectivity of 4,4'-methylene bis(cyclohexylamine) (PACM) prepared in this comparative example was 70-80%.

The analysis of the tail gas was as follows: Carbon monoxide (CO) was about 2 ppm, and methane gas (CH$_4$) was about 0.03%. The above hydrogenation reaction conditions, gas chromatography analysis results and tail gas analysis results are shown in Table 1.

Comparative Example 2

Preparation and product analysis of 4,4'-methylene bis(cyclohexylamine)

First, 7 mL of catalyst A (20-30 mesh) prepared in Preparation Example 1 was weighed, which contained 4.0% Ru and 1.0% Rh. Next, the catalyst was placed in a fixed-bed reactor, and 4,4'-methylenedianiline (MDA) was hydrogenated in a continuous trickle-bed mode to prepare 4,4'-methylene bis(cyclohexylamine) (PACM).

The conditions of the hydrogenation reaction were as follows: Tetrahydrofuran (THF) was used as a solvent. The concentration of 4,4'-methylenedianiline (MDA) (MDA$_{100}$;

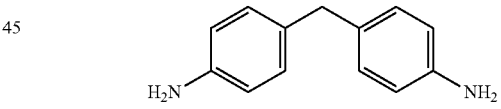

) (purchased from Shuang Bang Industrial Corp.) was 25.0 wt %. The liquid flow rate was 4.5 mL/h. The reaction temperature was 130° C. The reaction pressure was 70-75 bar. The hydrogen flow rate was 80-100 mL/m.

The analysis results of the gas chromatography analyzer were as follows: The conversion rate of 4,4'-methylenedianiline (MDA) was 100% (no monocyclic hydrogenated intermediate (H6MDA)). The yield of 4,4'-methylene bis(cyclohexylamine) (PACM) was about 70%, wherein the ratio of (trans, trans)-PACM was approximately 20%. The ratio of the self-coupling by-products was 12-20% (GC retention time at 40 minutes). The ratio of the coupling by-products of the products and cyclohexylamine was 0% (GC retention time at 25 minutes). The selectivity of 4,4'-methylene bis(cyclohexylamine) (PACM) prepared in this comparative example was 60-70%.

The analysis of the tail gas was as follows: Carbon monoxide (CO) was about 250-300 ppm, and methane gas ($CH_4$) was about 1-2%. The above hydrogenation reaction conditions, gas chromatography analysis results and tail gas analysis results are shown in Table 1.

TABLE 1

| Examples/ Com. Examples | Catalysts | Feeding | Self-coupling | coupling with cyclo-hexylamine | PACM selectivity | Tail gas CO (ppm) $CH_4$ (%) |
|---|---|---|---|---|---|---|
| Example 1 | B | 25% MDA/CHA | n.a. | 3-5% | 86-90% | ≤2 ppm; ≤0.03% |
| Example 2 | C | 25% MDA/CHA | n.a. | 2-3% | ≥90% | ≤2 ppm; ≤0.03% |
| Example 3 | D | 25% MDA/CHA | n.a. | ~2% | ≥90% | ≤2 ppm; ≤0.03% |
| Example 4 | C | 25% MDA/PACM | n.a | n.a | ≥95% | ≤2 ppm; ≤0.03% |
| Com. Example 1 | A | 25% MDA/CHA | n.a. | 10-16% | 70-80% | ≤2 ppm; ≤0.03% |
| Com. Example 2 | A | 25% MDA/THF | 12-20% | n.a. | 60-70% | 250-300 ppm; 1-2% |

Example 5

Preparation and Product Analysis of Hydrogenated 4,4'-Methylene-Bis(2-Methyl-6-Ethylaniline) (H-MED)

First, 7 mL of catalyst D (20-30 mesh) prepared in Preparation Example 4 was weighed, which contained 4.0% Ru and 1.0% Rh. Next, the catalyst was placed in a fixed-bed reactor, and 4,4'-methylene-bis(2-methyl-6-ethylaniline) (MED) was hydrogenated in a continuous trickle-bed mode to prepare hydrogenated 4,4'-methylene-bis(2-methyl-6-ethylaniline) (H-MED).

The conditions of the hydrogenation reaction were as follows: Tetrahydrofuran (THF) was used as a solvent and 5.0 wt % of 2-ethyl-6-methylaniline (2E6M-aniline) was added therein. The concentration of 4,4'-methylene-bis(2-methyl-6-ethylaniline) (MED;

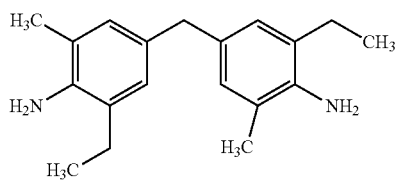

) (purchased from Shuang Bang Industrial Corp.) was 10.0 wt %. The liquid flow rate was 7.20 mL/h. The reaction temperature was 132° C. The reaction pressure was 70 bar. The hydrogen flow rate was 60-100 mL/m.

The analysis results of the gas chromatography analyzer were as follows: The conversion rate of 4,4'-methylene-bis(2-methyl-6-ethylaniline) (MED) was 100% (0.56% of monocyclic hydrogenated intermediate (H6MDA)). The yield of hydrogenated 4,4'-methylene-bis(2-methyl-6-ethylaniline) (H-MED) was about 99%, wherein the ratio of the self-coupling by-products was 0% (GC retention time at 40 minutes). The selectivity of hydrogenated 4,4'-methylene-bis(2-methyl-6-ethylaniline) (H-MED) prepared in this example was 98.7%. The results are shown in Table 2.

Example 6

Preparation and Product Analysis of 3,3'-Dimethyl-4,4'-Methylene Bis(Cyclohexylamine) (DMDC)

First, 7 mL of catalyst D (20-30 mesh) prepared in Preparation Example 4 was weighed, which contained 4.0% Ru and 1.0% Rh. Next, the catalyst was placed in a fixed-bed reactor, and 3,3'-dimethyl-4,4'-diaminodiphenylmethane (MDT) was hydrogenated in a continuous trickle-bed mode to prepare 3,3'-dimethyl-4,4'-methylene bis(cyclohexylamine) (DMDC).

The conditions of the hydrogenation reaction were as follows: Tetrahydrofuran (THF) was used as a solvent and 5.0 wt % of cyclohexylamine (CHA) was added therein. The concentration of 3,3'-dimethyl-4,4'-diaminodiphenylmethane (MDT;

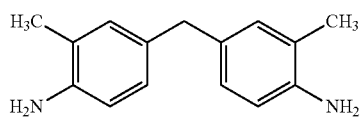 [SMILES: Cc1cc(Cc2ccc(N)c(C)c2)ccc1N]

) (purchased from Shuang Bang Industrial Corp.) was 10.0 wt %. The liquid flow rate was 7.20 mL/h. The reaction temperature was 132° C. The reaction pressure was 70 bar. The hydrogen flow rate was 60-100 mL/m.

The analysis results of the gas chromatography analyzer were as follows: The conversion rate of 3,3'-dimethyl-4,4'-diaminodiphenylmethane (MDT) was 100% (no monocyclic hydrogenated intermediate (H6MDA)). The yield of 3,3'-dimethyl-4,4'-methylene bis(cyclohexylamine) (DMDC) was about 97-98%, wherein the ratio of the self-coupling by-products was 0% (GC retention time at 40 minutes). The ratio of the coupling by-products of the products and cyclohexylamine was about 0.2-0.6% (GC retention time at 26 minutes). The selectivity of 3,3'-dimethyl-4,4'-methylene bis(cyclohexylamine) (DMDC) prepared in this example was 97.8%. The results are shown in Table 2.

Example 7

Preparation and Product Analysis of 3,3'-Dimethyl-4,4'-Methylene Bis(Cyclohexylamine) (DMDC)

First, 7 mL of catalyst D (20-30 mesh) prepared in Preparation Example 4 was weighed, which contained 4.0% Ru and 1.0% Rh. Next, the catalyst was placed in a fixed-bed reactor, and 3,3'-dimethyl-4,4'-diaminodiphenylmethane (MDT) was hydrogenated in a continuous trickle-bed mode to prepare 3,3'-dimethyl-4,4'-methylene bis(cyclohexylamine) (DMDC).

The conditions of the hydrogenation reaction were as follows: Tetrahydrofuran (THF) was used as a solvent and 5.0 wt % of aniline (AN) was added therein. The concentration of 3,3'-dimethyl-4,4'-diaminodiphenylmethane (MDT;

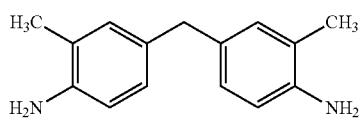

) (purchased from Shuang Bang Industrial Corp.) was 10.0 wt %. The liquid flow rate was 7.20 mL/h. The reaction temperature was 132° C. The reaction pressure was 70 bar. The hydrogen flow rate was 60-80 mL/m.

The analysis results of the gas chromatography analyzer were as follows: The conversion rate of 3,3'-dimethyl-4,4'-diaminodiphenylmethane (MDT) was 100% (no monocyclic hydrogenated intermediate (H6MDA)). The yield of 3,3'-dimethyl-4,4'-methylene bis(cyclohexylamine) (DMDC) was about 98%, wherein the ratio of the self-coupling by-products was 0% (GC retention time at 40 minutes). The ratio of the coupling by-products of the products and cyclohexylamine was about 0.3-0.5% (GC retention time at 26 minutes). The selectivity of 3,3'-dimethyl-4,4'-methylene bis(cyclohexylamine) (DMDC) prepared in this example was 98.1%. The results are shown in Table 2.

Example 8

Preparation and Product Analysis of 3,3'-Dimethyl-4,4'-Methylene Bis(Cyclohexylamine) (DMDC)

First, 7 mL of catalyst D (20-30 mesh) prepared in Preparation Example 4 was weighed, which contained 4.0% Ru and 1.0% Rh. Next, the catalyst was placed in a fixed-bed reactor, and 3,3'-dimethyl-4,4'-diaminodiphenylmethane (MDT) was hydrogenated in a continuous trickle-bed mode to prepare 3,3'-dimethyl-4,4'-methylene bis(cyclohexylamine) (DMDC).

The conditions of the hydrogenation reaction were as follows: Tetrahydrofuran (THF) was used as a solvent and 5.0 wt % of o-toluidine was added therein. The concentration of 3,3'-dimethyl-4,4'-diaminodiphenylmethane (MDT;

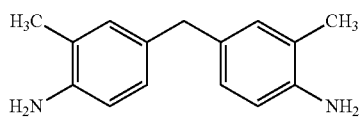 [SMILES: Cc1cc(Cc2ccc(N)c(C)c2)ccc1N]

) (purchased from Shuang Bang Industrial Corp.) was 10.0 wt %. The liquid flow rate was 7.20 mL/h. The reaction temperature was 132° C. The reaction pressure was 70 bar. The hydrogen flow rate was 60-100 mL/m.

The analysis results of the gas chromatography analyzer were as follows: The conversion rate of 3,3'-dimethyl-4,4'-diaminodiphenylmethane (MDT) was 100% (0.09% of monocyclic hydrogenated intermediate (H6MDA)). The yield of 3,3'-dimethyl-4,4'-methylene bis(cyclohexylamine) (DMDC) was about 97-98%, wherein the ratio of the self-coupling by-products was 0% (GC retention time at 40 minutes). The ratio of the coupling by-products of the products and o-toluidine was about 0.4-0.5% (GC retention time at 26 minutes). The selectivity of 3,3'-dimethyl-4,4'-methylene bis(cyclohexylamine) (DMDC) prepared in this example was 97.5%. The results are shown in Table 2.

Example 9

Preparation and Product Analysis of 4,4'-Methylene Bis(Cyclohexylamine) (PACM)

First, 7 mL of catalyst D (20-30 mesh) prepared in Preparation Example 4 was weighed, which contained 4.0% Ru and 1.0% Rh. Next, the catalyst was placed in a fixed-bed reactor, and 4,4'-methylenedianiline (MDA) was hydrogenated in a continuous trickle-bed mode to prepare 4,4'-methylene bis(cyclohexylamine) (PACM).

The conditions of the hydrogenation reaction were as follows: Tetrahydrofuran (THF) was used as a solvent and 5.0 wt % of aniline (AN) was added therein. The concentration of 4,4'-methylenedianiline (MDA) (MDA$_{96}$;

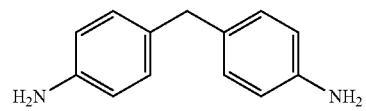 [SMILES: Nc1ccc(Cc2ccc(N)cc2)cc1]

) (purchased from Shuang Bang Industrial Corp.) was 10.0 wt %. The liquid flow rate was 6.3 mL/h. The reaction temperature was 115° C. The reaction pressure was 70 bar. The hydrogen flow rate was 80-100 mL/m.

The analysis results of the gas chromatography analyzer were as follows: The conversion rate of 4,4'-methylenedianiline (MDA) was 100% (no monocyclic hydrogenated intermediate (H6MDA)). The yield of 4,4'-methylene bis(cyclohexylamine) (PACM) was about 93-95%, wherein the ratio of (trans, trans)-PACM was approximately 20-22%. The ratio of the self-coupling by-products was 0% (GC retention time at 40 minutes). The ratio of the coupling by-products of the products and cyclohexylamine was about 3.3-3.5% (GC retention time at 25 minutes). The selectivity of 4,4'-methylene bis(cyclohexylamine) (PACM) prepared in this example was 95%. The results are shown in Table 2.

Comparative Example 3

Preparation and Product Analysis of 4,4'-Methylene Bis(Cyclohexylamine) (PACM)

First, 7 mL of catalyst D (20-30 mesh) prepared in Preparation Example 4 was weighed, which contained 4.0% Ru and 1.0% Rh. Next, the catalyst was placed in a fixed-bed reactor, and 4,4'-methylenedianiline (MDA) was hydrogenated in a continuous trickle-bed mode to prepare 4,4'-methylene bis(cyclohexylamine) (PACM).

The conditions of the hydrogenation reaction were as follows: Tetrahydrofuran (THF) was used as a solvent. The concentration of 4,4'-methylenedianiline (MDA) (MDA$_{96}$;

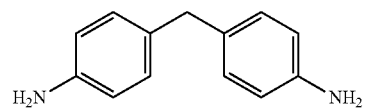

) (purchased from Shuang Bang Industrial Corp.) was 10.0 wt %. The liquid flow rate was 6.3 mL/h. The reaction temperature was 110-115° C. The reaction pressure was 65-70 bar. The hydrogen flow rate was 80-100 mL/m.

The analysis results of the gas chromatography analyzer were as follows: The conversion rate of 4,4'-methylenedianiline (MDA) was 100% (no monocyclic hydrogenated intermediate (H6MDA)). The yield of 4,4'-methylene bis (cyclohexylamine) (PACM) was about 90%, wherein the ratio of (trans, trans)-PACM was approximately 21%. The ratio of the self-coupling by-products was 8% (GC retention time at 40 minutes). The selectivity of 4,4'-methylene bis (cyclohexylamine) (PACM) prepared in this example was 90%. The results are shown in Table 2.

TABLE 2

| Examples/ Com. Examples | Catalysts | Feeding | Selectivity (%) | Intermediate products (%) | Conversion rate (%) | Yield (%) |
|---|---|---|---|---|---|---|
| Example 5 | D | 10% MED/ 5% 2E6M-aniline/ THF | 98.7 | 0.56 | 100 | 99.29 |
| Example 6 | D | 10% MDT/ 5% CHA/ THF | 97.8 | 0 | 100 | 97.87 |
| Example 7 | D | 10% MDT/ 5% aniline/ THF | 98.1 | 0 | 100 | 98.09 |
| Example 8 | D | 10% MDT/ 5% o-toluidine/ THF | 97.5 | 0.09 | 100 | 97.54 |
| Example 9 | D | 10% MDA/ 5% aniline/ THF | 95 | 0 | 100 | 95 |
| Com. Example 3 | D | 10% MDA/ THF | 90 | 0 | 100 | 90 |

From the results in Table 1, it can be seen that when the solvent added to the hydrogenation catalyst system was merely a non-amine solvent (such as tetrahydrofuran (THF)) or the content of the magnesium oxide in the carrier was less than 10% (Comparative Examples 1 and 2), more coupling by-products, lower product selectivity, or high levels of carbon monoxide and methane gas (poisoning catalyst activity) in the tail gas were generated, causing difficulties in hydrogen recovery and process complexity, increasing costs of investment and solvent. However, when the solvent added to the hydrogenation catalyst system was an organic amine solvent (such as cyclohexylamine or 4,4'-methylene bis (cyclohexylamine)) or the content of the magnesium oxide in the carrier was increased (12% or more) (Examples 1-4), not only the self-coupling by-products and the coupling by-products of the products and cyclohexylamine can be greatly reduced, but also the tail gas contains only a relatively low proportion of carbon monoxide and methane gas, and can effectively improve the selectivity of 4,4'-methylene bis(cyclohexylamine) to more than 95%.

From the results in Table 2, it can be seen that when the solvent added to the hydrogenation catalyst system was merely a non-amine solvent (such as tetrahydrofuran (THF)) (Comparative Example 3), the product selectivity was dropped significantly. However, in addition to tetrahydrofuran (THF), when an organic amine solvent (such as aniline, cyclohexylamine or o-toluidine) was further added to the hydrogenation catalyst system (Examples 5-9), not only the self-coupling by-products and the coupling by-products of the products and cyclohexylamine can be reduced, but also can effectively improve the selectivity of 4,4'-methylene bis(cyclohexylamine) derivatives to approach 99%.

While the disclosure has been described by way of example and in terms of the preferred embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A catalyst composition for hydrogenating 4,4'-methylenedianiline derivatives, comprising:
    a carrier comprising aluminum oxide and magnesium oxide, the carrier having a surface and an interior, wherein the magnesium oxide in the carrier has a weight percentage from 12% to 30%;
    a rhodium-ruthenium active layer loaded on the surface of the carrier; and
    a solvent comprising an organic amine.

2. The catalyst composition for hydrogenating 4,4'-methylenedianiline derivatives as claimed in claim 1, wherein the magnesium oxide has a concentration which exhibits a decreasing gradient distribution from the surface to the interior of the carrier.

3. The catalyst composition for hydrogenating 4,4'-methylenedianiline derivatives as claimed in claim 1, wherein the carrier has a specific surface area from 150 $m^2/g$ to 250 $m^2/g$.

4. The catalyst composition for hydrogenating 4,4'-methylenedianiline derivatives as claimed in claim 1, wherein the weight percentage of the magnesium oxide in the carrier is in a range from 14% to 25%.

5. The catalyst composition for hydrogenating 4,4'-methylenedianiline derivatives as claimed in claim 1, wherein the interior of the carrier consists of the aluminum oxide, and the surface of the carrier consists of magnesium aluminum oxide.

6. The catalyst composition for hydrogenating 4,4'-methylenedianiline derivatives as claimed in claim 5, wherein magnesium oxide and aluminum oxide in the magnesium aluminum oxide have a weight ratio from 2:1 to 1:2.

7. The catalyst composition for hydrogenating 4,4'-methylenedianiline derivatives as claimed in claim 5, wherein the magnesium aluminum oxide in the carrier has a weight percentage from 20% to 50%.

8. The catalyst composition for hydrogenating 4,4'-methylenedianiline derivatives as claimed in claim 1, wherein rhodium and ruthenium in the rhodium-ruthenium active layer have a weight ratio from 40:60 to 10:90.

9. The catalyst composition for hydrogenating 4,4'-methylenedianiline derivatives as claimed in claim 1, wherein the rhodium-ruthenium active layer and the carrier have a weight ratio from 1:24 to 1:16.

10. The catalyst composition for hydrogenating 4,4'-methylenedianiline derivatives as claimed in claim 1, wherein the organic amine comprises aniline, cyclohexylamine, dicyclohexyl amine, o-toluidine, 2-methylaniline, 2-methylcyclohexylamine, 2,6-dimethylaniline, 2,6-dimethylcyclohexylamine, 2-ethyl-6-methyl aniline, 2-ethyl-6-methylcyclohexylamine, 4,4'-methyl ene bis(cyclohexylamine) derivatives, or a combination thereof.

11. The catalyst composition for hydrogenating 4,4'-methylenedianiline derivatives as claimed in claim 10, wherein the 4,4'-methylene bis(cyclohexylamine) derivatives are represented by formula (I):

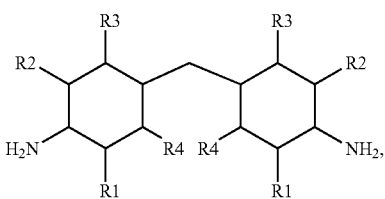

wherein R1, R2, R3 and R4, independently, comprise H, CH₃, C₂H₅ or C₃H₇.

12. The catalyst composition for hydrogenating 4,4'-methylenedianiline derivatives as claimed in claim 1, wherein the solvent further comprises tetrahydrofuran (THF).

13. The catalyst composition for hydrogenating 4,4'-methylenedianiline derivatives as claimed in claim 1, wherein the solvent does not comprise tetrahydrofuran, alcohols or ethers.

14. The catalyst composition for hydrogenating 4,4'-methylenedianiline derivatives as claimed in claim 1, wherein the 4,4'-methylenedianiline derivatives comprise substituted or unsubstituted 4,4'-methylenedianiline.

15. A method for preparing 4,4'-methylene bis(cyclohexylamine) derivatives, comprising:
   placing a catalyst composition for hydrogenating 4,4'-methylenedianiline derivatives as claimed in claim 1 in a reactor; and
   introducing 4,4'-methylenedianiline derivatives and hydrogen into the reactor to proceed a hydrogenation reaction to prepare 4,4'-methylene bis(cyclohexylamine) derivatives.

16. The method for preparing 4,4'-methylene bis(cyclohexylamine) derivatives as claimed in claim 15, wherein the reactor comprises a continuous reactor.

17. The method for preparing 4,4'-methylene bis(cyclohexylamine) derivatives as claimed in claim 15, wherein the reactor comprises a trickle-bed reactor, a bubble-cap column reactor, or a loop reactor.

18. The method for preparing 4,4'-methylene bis(cyclohexylamine) derivatives as claimed in claim 15, wherein the hydrogenation reaction has a hydrogen pressure from 60 bar to 80 bar.

19. The method for preparing 4,4'-methylene bis(cyclohexylamine) derivatives as claimed in claim 15, wherein the hydrogenation reaction has a temperature from 100° C. to 160° C.

20. The method for preparing 4,4'-methylene bis(cyclohexylamine) derivatives as claimed in claim 15, wherein the 4,4'-methylenedianiline derivatives are represented by formula (II):

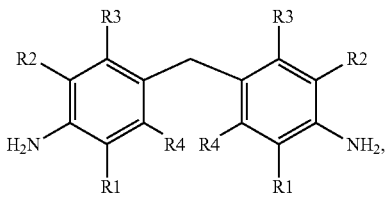

wherein R1, R2, R3 and R4, independently, comprise H, CH₃, C₂H₅ or C₃H₇.

* * * * *